United States Patent [19]
Yamada et al.

[11] Patent Number: 5,641,357
[45] Date of Patent: Jun. 24, 1997

[54] APPARATUS FOR CHECKING GLUE APPLICATION STATE

[75] Inventors: Takeo Yamada, Yokohama; Kazuo Kawamura; Hironobu Yoshikawa, both of Hachioji; Minoru Moriya, Uenohara-machi; Toshiyuki Kasahara, Hino, all of Japan

[73] Assignee: Nireco Corporation, Tokyo, Japan

[21] Appl. No.: 540,702

[22] Filed: Oct. 11, 1995

[30] Foreign Application Priority Data

Oct. 25, 1994 [JP] Japan .................................. 6-260089

[51] Int. Cl.⁶ ...................................................... B05C 5/00
[52] U.S. Cl. ............................ 118/665; 118/676; 118/712
[58] Field of Search ................................ 118/665, 676, 118/712; 427/8; 156/378, 379

[56] References Cited

U.S. PATENT DOCUMENTS

| 4,389,969 | 6/1983 | Johnson .................................... 118/665 |
| 5,322,566 | 6/1994 | Satoh et al. ............................... 118/712 |

FOREIGN PATENT DOCUMENTS

| 1348982 | 3/1974 | United Kingdom . |
| 2086585 | 4/1982 | United Kingdom . |

*Primary Examiner*—Laura Edwards
*Attorney, Agent, or Firm*—Lowe, Price, LeBlanc & Becker

[57] ABSTRACT

The invention provides an apparatus for checking glue application state of almost electrically non-conductive object to which an electrically conductive glue is applied on either side thereof, including (a) an electrode for transmitting high frequency therefrom, (b) a pair of receiving electrodes each spaced from the high frequency transmitting electrode at its opposite sides, (c) a detector head for aligning distal ends of the electrodes at almost the same level and shielding the electrodes from one another, (d) a high frequency generator for supplying high frequency to the high frequency transmitting electrode, (e) a gluing condition detector for detecting gluing condition of the object on the basis of a difference in output between the receiving electrodes, and (f) a position adjuster for adjusting relative position between a glue applied to the object and each of the electrodes. Outputs of the receiving electrodes contains almost the same amount of noise, and thus it is possible to eliminate noise by calculating a difference in output between the receiving electrodes. Thus, the present invention ensures more accurate detection of the gluing condition of an object.

5 Claims, 11 Drawing Sheets

APPARATUS FOR CHECKING GLUE APPLICATION STATE

BACKGROUND OF THE INVENTION

1. Field of the Invention

The invention relates to an apparatus for checking glue application state of an object to which a glue has been applied at a bottom surface thereof.

2. Description of the Related Art

In gluing processes for sack machines and collators, gluing is carried out by means of a glue applicator nozzle or a glue applicator wheel. The gluing needs to be tested as to whether the gluing has been carried out properly.

One of methods of testing whether glue is certainly applied to an object is a method in which two electrodes are disposed at the opposite sides of a glued object, and a change in electrostatic capacity between the two electrodes are detected in dependence on presence or absence of a glue. In another method, a glue is colored, and whether a glue is present or absent is detected by a light reflected from the glue. Japanese Unexamined Patent Public Disclosure No. 60-99641 has suggested still another glue application checking method which includes the steps of inserting a carton to which a glue is applied between a transmitting electrode plate and a receiving electrode plate, transmitting and receiving high-frequency waves between the two electrodes, and monitoring glue application state in accordance with attenuation of the high-frequency waves received by the receiving electrode.

In the method utilizing electrostatic capacity, since the two electrodes are facing with a glued object being disposed therebetween, one of the electrodes faces to a surface of the object onto which a glue is applied. Thus, a glue may adhere to a surface of the electrode facing to the surface of the object onto which the glue is applied. If a glue is adhered to an electrode, the variation of detected electrostatic capacity is remarkably increased, and hence it is no longer possible to detect a change in the electrostatic capacity. In addition, the detected electrostatic capacity is also influenced by humidity, and thus it is quite difficult to stably detect whether a glue is present or absent. The optical method needs a glue to be colored. In the method suggested by Japanese Unexamined Patent Public Disclosure No. 60-99641 in which a variation in voltage of the receiving electrode caused by a glue dispensed between the transmitting and receiving electrodes is to be detected, since an object to be glued has to be passed between the two electrodes, a space between the electrodes has to be large, and hence it is difficult to increase detection accuracy about whether a glue is present or absent.

The assignee has already suggested in Japanese Unexamined Patent Public Disclosure No. 5-340892 that a glue applicator nozzle is used as an electrode, and one more electrode is disposed so that an object to be tested is situated between the glue applicator nozzle and the electrode, and also suggested in Japanese Patent Application No. 5-056235 (U.S. Pat. No. 5,322,566) that a glue applicator nozzle is used as an electrode, and one more electrode is disposed at the same side of the glue applicator nozzle with respect to an object to be tested. However, even if a distance between the electrodes is shortened by the above mentioned suggestion, a signal representing whether a glue is present or absent is still small, and in addition, a noise signal is still relatively large because of temperature variation, humidity variation, and variation of a position of metal material disposed in the vicinity of a glue applicator nozzle, and hence it was difficult to obtain with high accuracy the signal representing whether a glue is present or absent. In addition, even by the above mentioned methods, it is impossible to check glue application state of an object glued by using a widely used glue applicator wheel.

SUMMARY OF THE INVENTION

In view of the problems as mentioned above, it is an object of the present invention to provide an apparatus for checking glue application state which has two receiving electrodes one of which mainly receives noise signals and the other of which receives both noise signals and signals from a glue, calculates a difference between outputs from these two receiving electrodes, and thereby makes it possible to obtain signals representing whether a glue is present or absent with less influence by noises and also with accuracy, and which can be applied to a check of glue application state of an object glued by using a glue applicator wheel.

The invention provides an apparatus for checking glue application state of almost electrically non-conductive object to which an electrically conductive glue is applied on either side thereof, the apparatus including (a) an electrode for transmitting high frequency therefrom, (b) a pair of receiving electrodes each spaced away from the high frequency transmitting electrode at its opposite sides, (c) a detector head for aligning distal ends of the electrodes at almost the same level and shielding the electrodes from one another, (d) a high frequency generator for supplying high frequency to the high frequency transmitting electrode, and (e) a glue application state detector for detecting glue application state of the object on the basis of a difference in output between the receiving electrodes.

The invention further provides an apparatus for checking glue application state of almost electrically non-conductive object to which an electrically conductive glue is applied on either side thereof, the apparatus including (a) an electrode for transmitting high frequency therefrom, (b) a pair of receiving electrodes each spaced away from the high frequency transmitting electrode at its opposite sides, (c) a detector head for aligning distal ends of the electrodes at almost the same level and shielding the electrodes from one another, (d) a high frequency generator for supplying high frequency to the high frequency transmitting electrode, (e) a glue application state detector for detecting glue application state of the object on the basis of a difference in output between the receiving electrodes, and (f) a position adjuster for adjusting relative position between a glue applied to the object and each of the electrodes.

In a preferred embodiment, the position adjuster adjusts the position of the glue to be applied to the object so that the glue is disposed closer to one of the receiving electrodes than to the middle between the high frequency transmitting electrode and the one of the receiving electrodes.

In another preferred embodiment, the position adjuster adjusts a distance between distal ends of the electrodes and a surface of the object to which the glue is to be applied.

The advantages obtained by the aforementioned present invention will be described hereinbelow.

While an object to which a glue is applied on a surface thereof is being fed below the detector head, the high frequency transmitting electrode transmits high frequency electromagnetic waves. Some of the electromagnetic waves are directly received into the receiving electrode, a part of the remaining electromagnetic waves are reflected by the glued object. Some of the reflected waves are directly received by the receiving electrodes, and the other produces an eddy current due to magnetic induction in small amount of moisture contained in the object and then is attenuated. If a distance between each of the electrodes and the object to be glued is over a predetermined value, the detection of glue application state is scarcely influenced by the reflection and induction. On the other hand, both the electromagnetic wave passing through an object and the electromagnetic wave coming to no contact with an object spatially spreads, and some of them enter the receiving electrodes. If a glue contains humidity and has conductivity, an electromagnetic wave produces an eddy current due to electromagnetic induction when the electromagnetic wave reaches the glue. The thus produced eddy current produces a magnetic field therearound. The magnetic field has a function to eliminate a magnetic field produced by the electromagnetic wave, and consumes energy because of electromagnetic induction. Thus, the electromagnetic wave is weakened in the vicinity of the glue to be detected. As a result, if a glue is brought near one of the receiving electrodes, electromagnetic waves received by the receiving electrode is reduced. Accordingly, it is possible to detect whether a glue is present or absent by calculating a difference in output between the receiving electrodes. An object to be glued may have slight conductivity due to humidity, but it is smaller than the conductivity of a glue, and thus is negligible. Since both of the receiving electrodes receive almost the same amount of noise, it is possible to eliminate influence exerted by the noise by calculating a difference in output between the receiving electrodes.

The relative position between the receiving electrodes and a glue applied to an object is adjusted so as to increase detection accuracy.

When a glue is disposed closer to one of the receiving electrodes than to the center between the high frequency transmitting electrode and the one of the receiving electrodes, the presence of a glue is clearly found in a difference in output between the receiving electrodes.

A smaller distance between the distal ends of the electrodes disposed below the detector head and an upper surface of an object to be glued makes a major portion of electromagnetic waves transmitted from the high frequency transmitting electrode to be reflected on an upper surface of an object to be glued and received into the receiving electrodes, thereby the signals representing whether a glue is present or absent being reduced to be relatively small. However, a larger distance between a surface of an object onto which a glue is applied and distal ends of the electrodes makes the signals representing whether a glue is present or absent to be small. Thus, a distance between the distal ends of the electrodes and the surface of the object onto which a glue is applied is determined so that the signal representing whether a glue is present or absent is maximized. For example, when a glue is applied to an object at its lower surface, the signal can be maximized by setting the distance between the lower surface of the object and the distal ends of the electrodes to be about 4 mm.

As is obvious from the foregoing description, in the apparatus in accordance with the invention, the receiving electrodes are disposed spaced away from the high frequency transmitting electrode, and when the glue is brought near one of the receiving electrodes, it is possible to detect whether a glue is applied to an object by calculating a difference in output between the receiving electrodes. Since the outputs of the receiving electrodes contain noises in almost the same amount, the noises can be removed by calculating a difference between the outputs of the receiving electrodes. Thus, it is now possible to check the glue application state with high accuracy.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained hereinbelow with reference to drawings.

Figure 1:
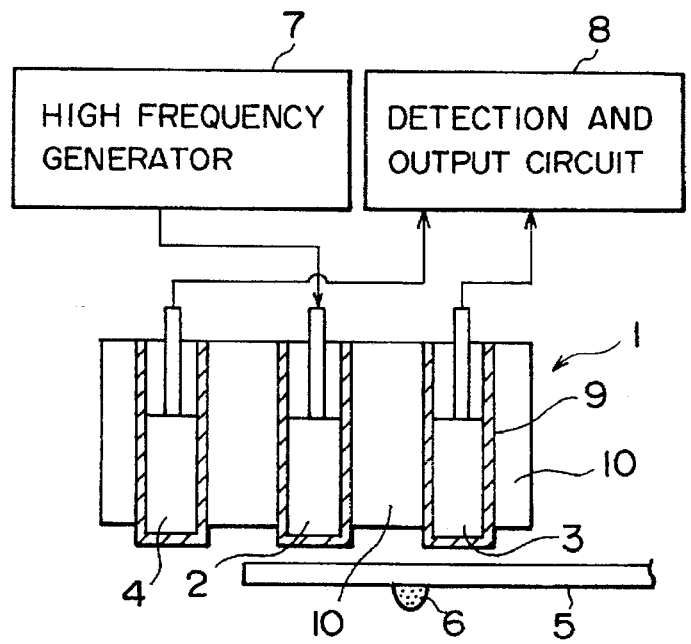
FIG. 1 is a schematic view illustrating the detector head.
Figure 2:
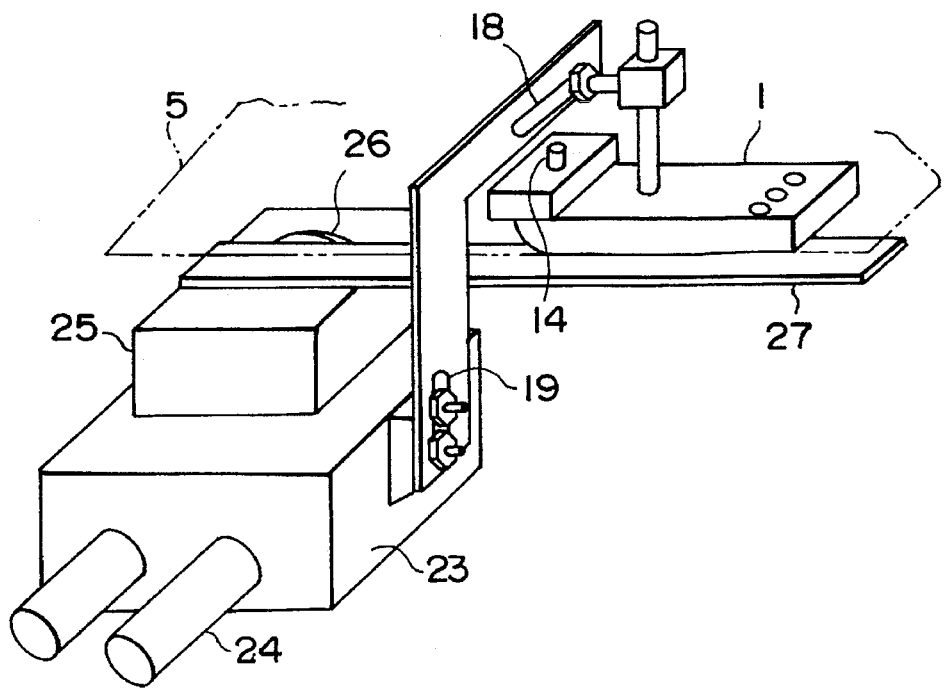
FIG. 2 is a perspective view of the apparatus in accordance with the first embodiment.
Figure 3:
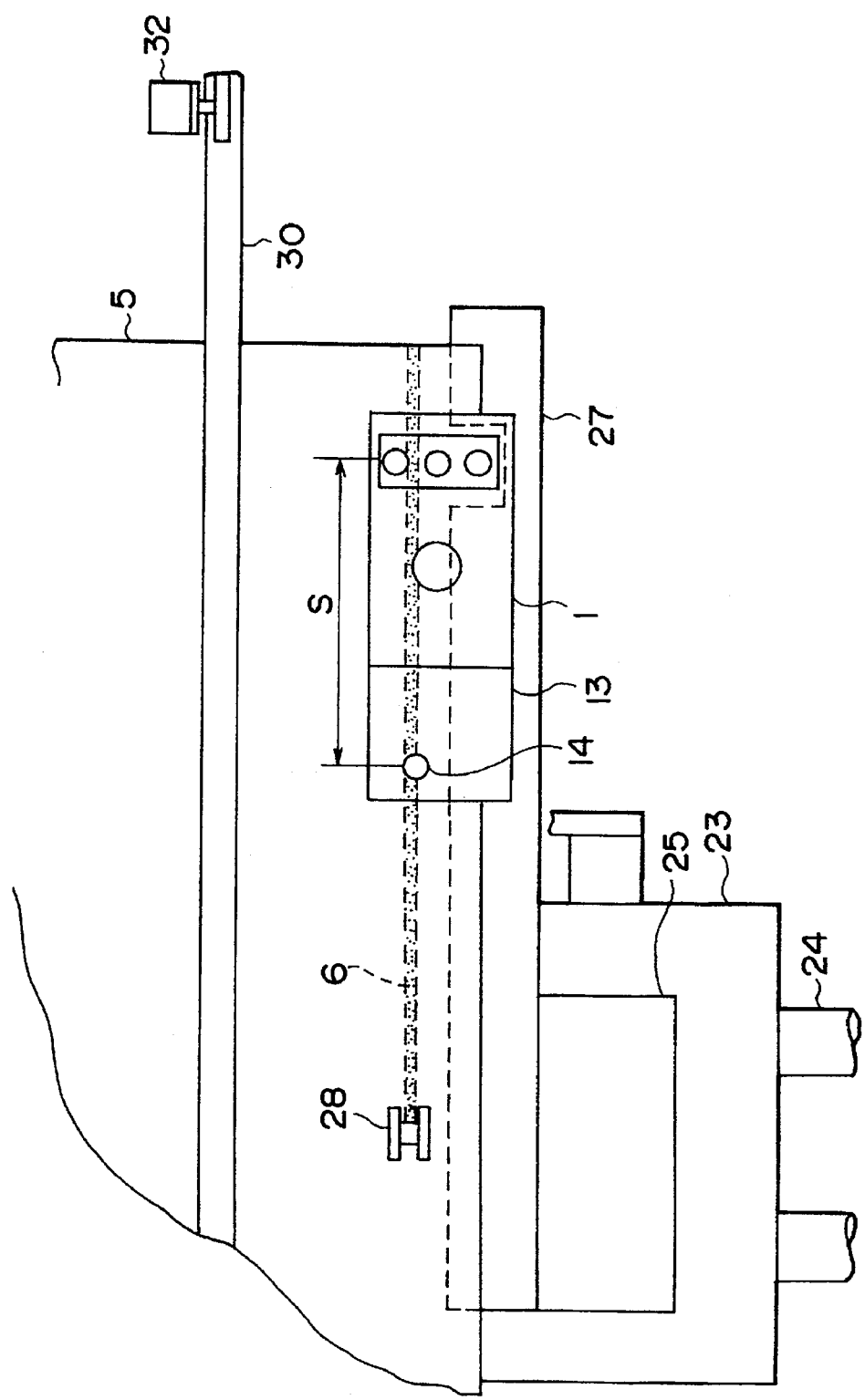
FIG. 3 is a plan view of the apparatus illustrated in FIG. 2.
Figure 4:
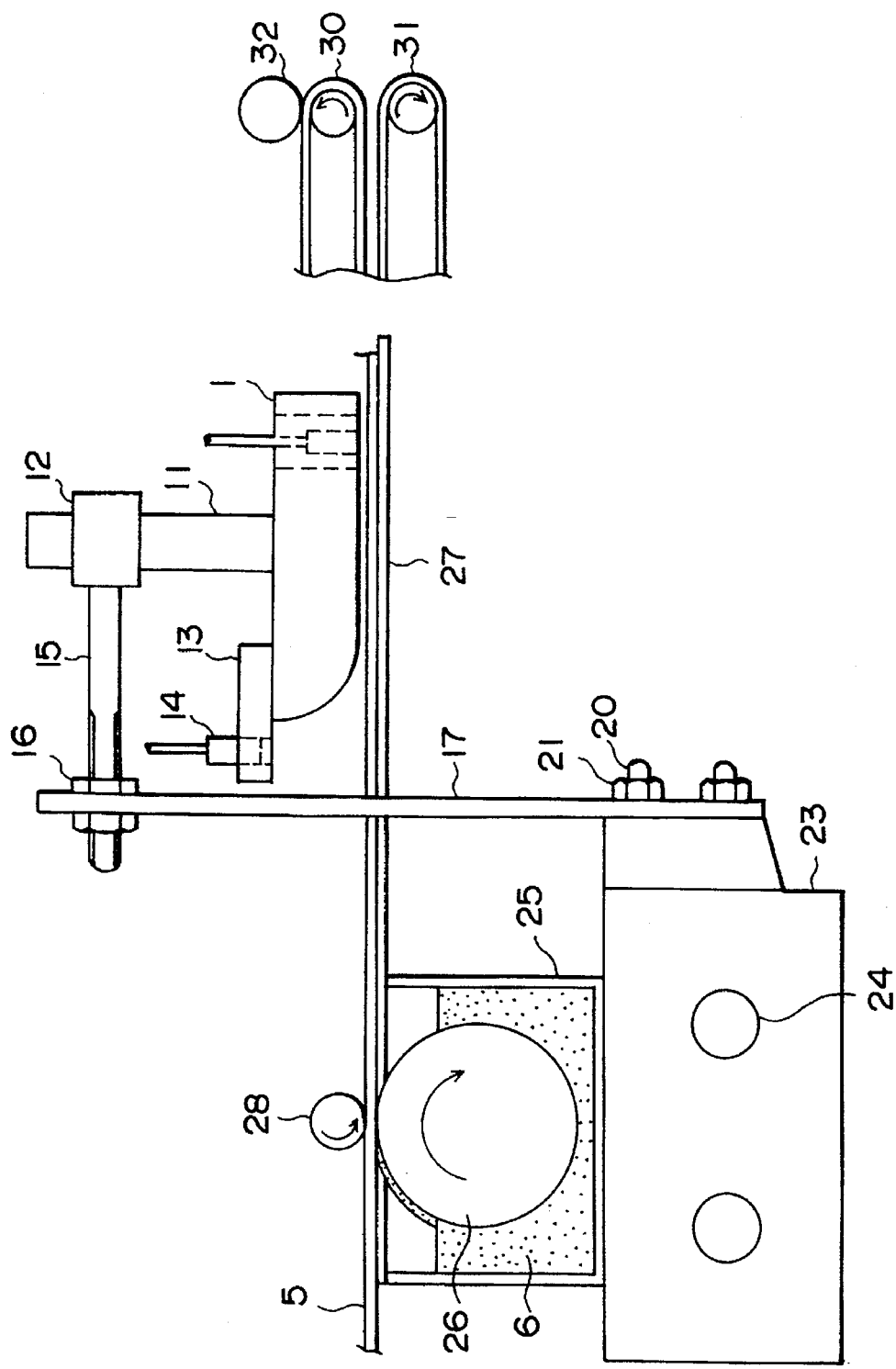
FIG. 4 is a side view of the apparatus illustrated in FIG. 2.

In the first embodiment, the apparatus for checking glue application state in accordance with the invention is applied to an apparatus for applying a glue to a carton. FIG. 1 is a schematic view of a detector head, FIG. 2 is a perspective view of an apparatus for checking glue application stage in accordance with the first embodiment, FIG. 3 is a plan view of the apparatus illustrated in FIG. 2, and FIG. 4 is a side view of the apparatus illustrated in FIG. 2. With reference to FIG. 1, a detector head 1 comprises a high frequency transmitting electrode 2, a receiving electrode 3 for detection, and a receiving electrode 4 to be used as a reference. The electrodes 2, 3 and 4 are surrounded in an insulator 9 which is electrically sealed with a grounded metal case 10. Each distal end of the electrodes projects from the shield 10 by about 1 mm. The insulator 9 is composed of resin, and hence is readily cleaned off a glue or dust. The receiving electrode 3 to be used for detection and the reference receiving electrode 4 are evenly spaced away from the high frequency transmitting electrode 2 at opposite sides of the electrode 2. Each of the electrodes 2 and 3 transmits and receives signals at the bottom thereof. The receiving electrode 3 for detection has the same structure as that of the reference receiving electrode 4. An object 5 to which a glue is to be applied comprises a carton. A glue 6 is applied to the carton along an edge of a lower of surface thereof. Among a variety of glues, the glue 6 is selected to contain humidity therein and have electrical conductivity. A high frequency generator 7 is in electrical connection with and supplies high frequency to the high frequency transmitting electrode 2, and the receiving electrode 3 for detection and the reference receiving electrode 4 are in electrical connection with a detection and output circuit 8 by which glue application state of the object 5 is detected.

With reference to FIGS. 2 to 4, at the center of the detector head 1 is disposed a pillar 11 having a metal fitting 12 fixed thereto at a distal end thereof. The detector head 1 has a support plate 13 secured thereto at an end opposite to the end at which the electrodes 2, 3, and 4 are disposed, which support plate 13 supports a sensor 14 for detecting the presence of the object. The sensor 14 detects whether the glued object 5 is being fed therebelow, and is spaced away from the electrodes 2, 3 and 4 by a distance S. A bolt 15 is fixedly secured to the metal fitting 12 at an end thereof, and is connected at the other end thereof to an end of an L-shaped arm 17 by means of a nut 16. The arm 17 is fixedly secured at a proximal end thereof to a base 23 by means of a bolt 20 and a nut 21. Each of openings 18 and 19 formed with the arm 17, through which the bolts 15 and 20 are to be inserted, has an elongated oval shape, and thus it is possible to horizontally and vertically move the detector head 1. If a place where the glue 6 is applied onto the object 5 and a thickness of the object 5 are determined in advance, the openings 18 and 19 are to be formed at a position to be determined in dependence on them, and thus need not to have an elongated oval shape.

On the base 23 is mounted a glue container 25. The base 23 is designed to be slidable by means of a guide rod 24 passing through the base 23, perpendicularly to a direction in which the carton 5 is to be fed. The slide movement of the base is manually carried out. In the glue container 25 is disposed a glue applicator wheel 26 which comes to contact with an lower surface of the carton 5, rotates as the carton 5 is fed, and applies the glue 6 onto the lower surface of the carton 5. Over the glue container 25 is disposed a guide plate 27 on an upper surface of which runs an edge of the carton 5, and which ensures that a lower surface of the carton 5 to which the glue is to be applied is spaced away by about 4 mm from the distal ends of the electrodes 2, 3 and 4 disposed below the detector head 1. It should be noted that a thickness of the insulators 9 covering the distal ends of the electrodes therewith is included in the distance 4 mm. A compression roll 28 is disposed above the glue applicator wheel 26, and cooperates with the glue applicator wheel 26 to interpose the carton 5 therebetween to thereby ensure glue application to the carton 5. Conveyer belts 30 and 31 interposes the carton 5 therebetween, and feed the carton 5 towards the detector head 1. The conveyer belt 30 is provided with an encoder 32 to measure a feeding distance of the carton 5. A length in which the glue 6 is applied to the carton 5 is calculated on the basis of the thus measured feeding distance.

The detector head 1 is positioned so that the glue 6 applied onto a lower surface of the carton 5 by the glue applicator wheel 26 passes between the high frequency transmitting electrode 2 and the receiving electrode 3 for detection along a route closer to the receiving electrode 3 than to the middle point between the high frequency transmitting electrode 2 and the receiving electrode 3. The adjustment of position of the detector head I is carried out by loosening the nut 16, moving the bolt 15 to an appropriate position, and fastening the nut 16.

Figure 5:
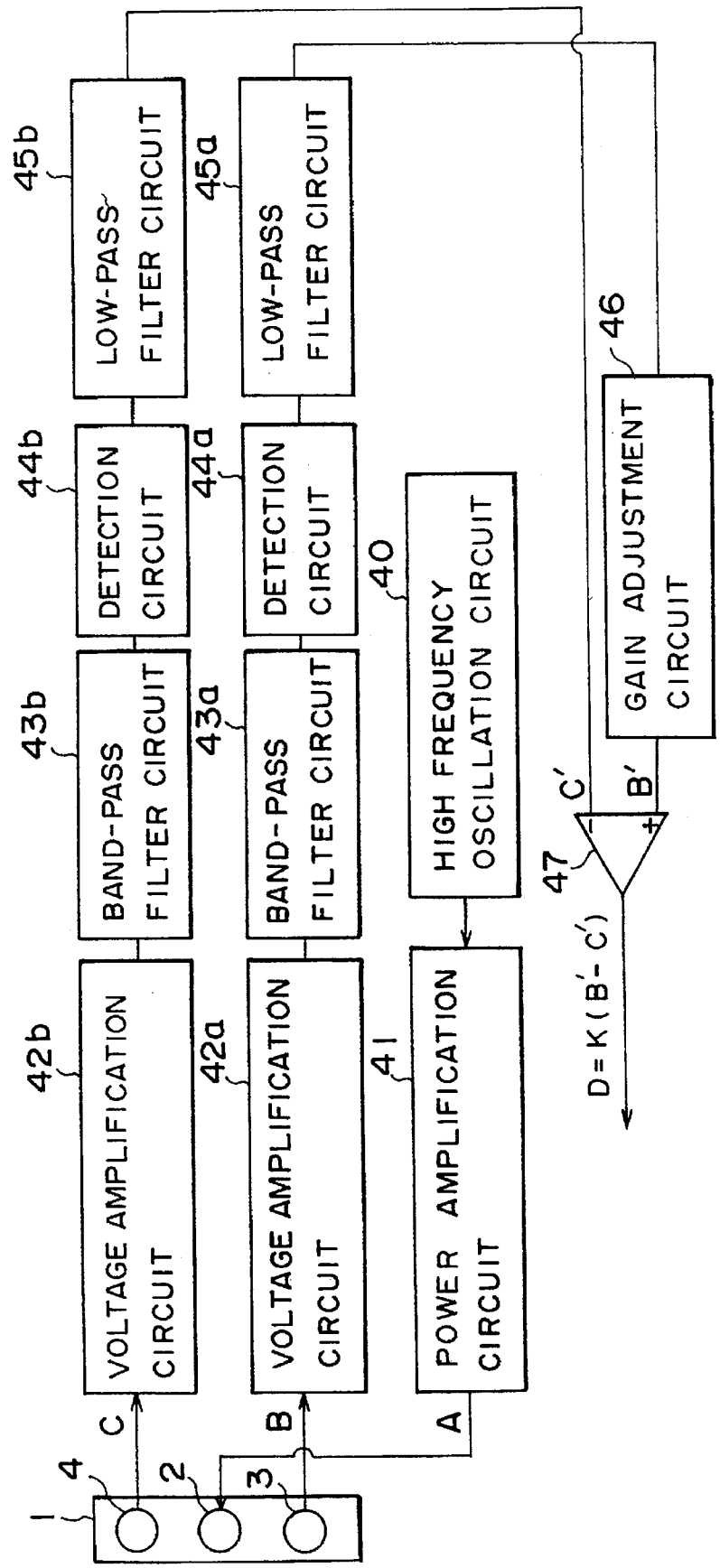
FIG. 5 is a block diagram of the high frequency generator and the detection and output circuit illustrated in FIG. 1.
Figure 6:
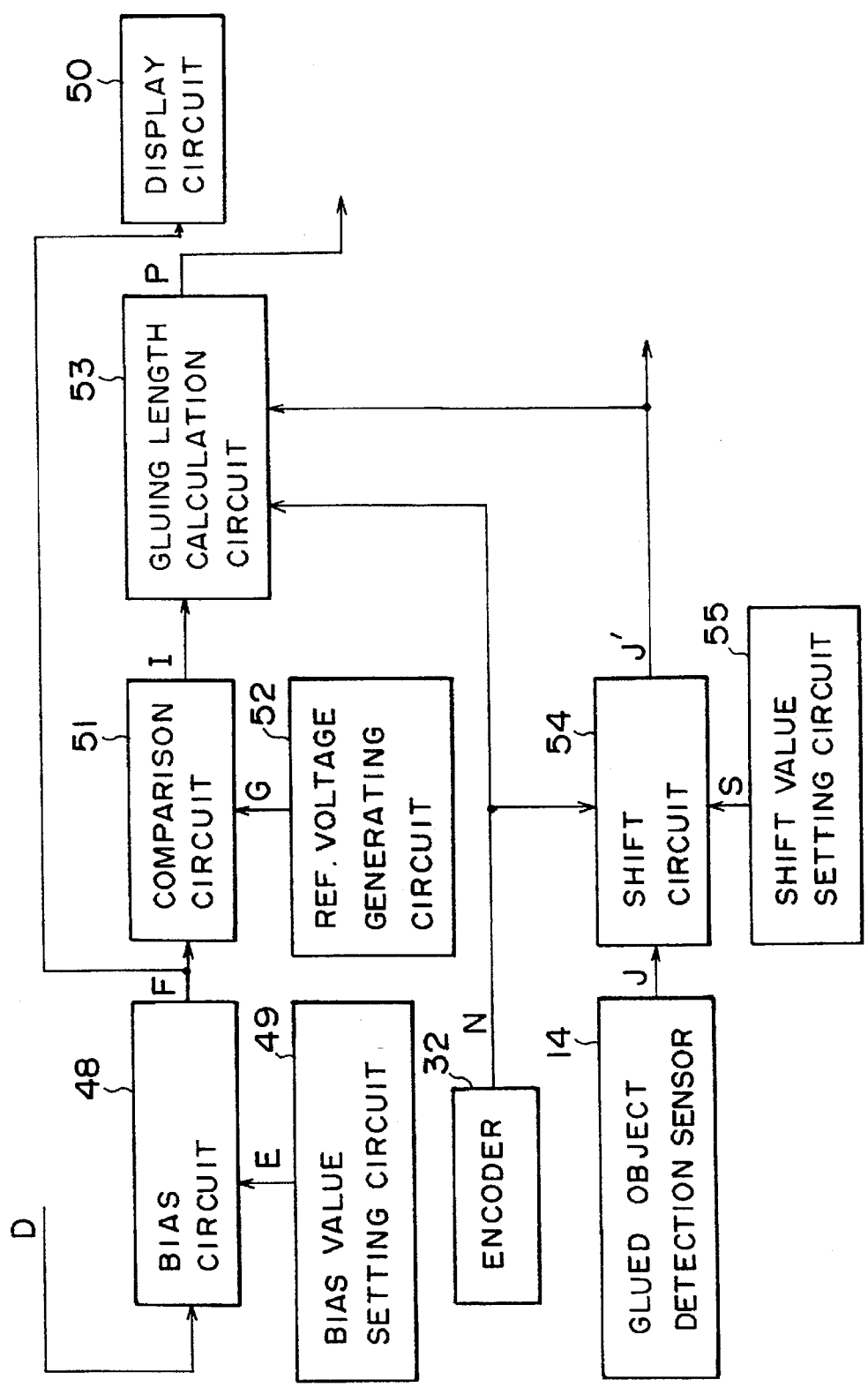
FIG. 6 is a block diagram of the detection and output circuit illustrated in FIG. 1.
Figure 7:
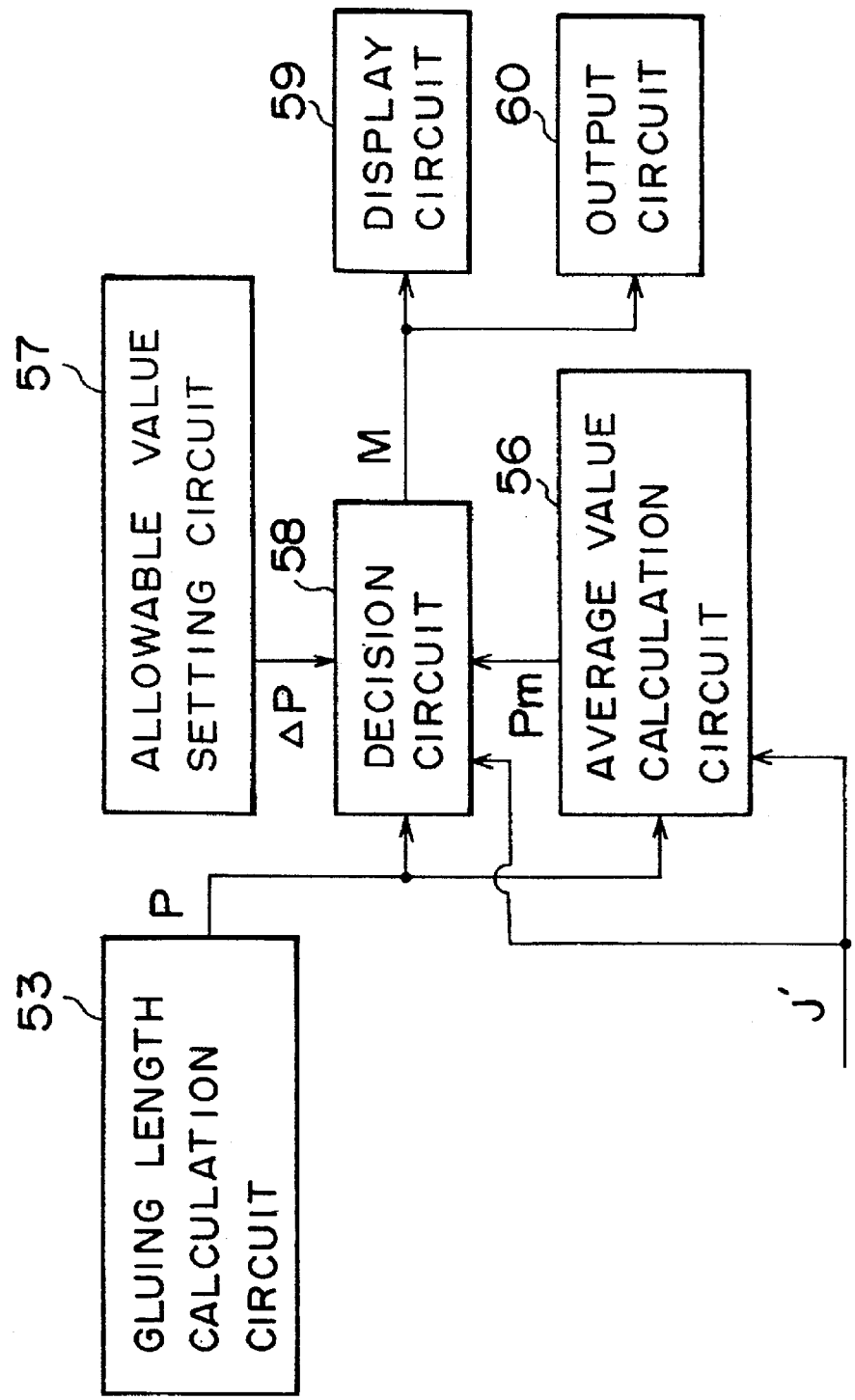
FIG. 7 is a block diagram of the detection and output circuit illustrated in FIG. 1.

FIGS. 5, 6 and 7 illustrate the detail of the high frequency generator 7 and the detection and output circuit 8 each illustrated in FIG. 1. With reference to FIG. 5, the high frequency generator comprises a high frequency oscillation circuit 40 which oscillates at a constant amplitude (for instance, 30 Vp-p) and a constant frequency (for instance, 500 KHz), and a power amplifying circuit 41 for amplifying the output of the high frequency oscillation circuit.

The detection and output circuit 8 has the structure as follows. The high frequency electromagnetic wave received by the receiving electrode 3 for detection and the reference receiving electrode 4 is amplified in voltage by voltage amplification circuits 42a and 42b, and then noises are removed by bandpass filter circuits 43a and 43b from the high frequency to thereby enhance the S/N ratio. Signals representing the presence of the glue 6 are taken out by detection circuits 44a and 44b, and then high frequency components are removed by low-pass filter circuits 45a and 45b.

A gain adjustment circuit 46 comprises an amplifier or a bias value setting circuit, and is a circuit for conforming output level of the low-pass filter circuits 45a and 45b to each other with the glue 6 being not applied to the object 5. A differential amplification circuit 47 amplifies a difference in output between the receiving electrode 3 for detection and the reference receiving electrode 4. The receiving electrodes 3 and 4 receive noises from the surrounding to almost the same degree, and have almost the same drift caused by temperature and humidity. However, since the receiving electrode 3 for detection receives smaller voltage than that of the reference receiving electrode 4 because of the presence of the glue 6, a difference in output between the receiving electrodes 3 and 4 indicates a signal from which the noise and drift are removed and which represents the presence of the glue. Output B of the receiving electrode 3 for detection turns into B' by passing from the voltage amplification circuit 42a to the gain adjustment circuit 46, while output C of the reference receiving electrode 4 turns into C' by passing from the voltage amplification circuit 42b to the low-pass filter 45b. A difference (B'–C') between these outputs is amplified by K times to thereby turn into a signal D.

With reference to FIG. 6, a bias circuit 48 applies a bias voltage to the signal D, when the signal D is to be displayed on the display circuit 50, so as to display the signal D at an appropriate position on a display. A bias value E is established by a bias value setting circuit 49. A comparison circuit 51 compares a value F, which is equal to a sum of the value D displayed on the display circuit 50 and a value E, with a reference value G produced by a reference voltage generating circuit 52. When the value F is equal to or smaller than the value G, the comparison circuit 51 transmits a high level signal as an output I representing that the glue 6 has been applied, while when the value F is over the value G, the comparison circuit 51 transmit a low level signal representing that the glue 6 has not been applied.

As having been explained with reference to FIG. 3, the encoder 32 measures a feeding distance of the carton 5, and transmits pulse signals N. The sensor 14 for detecting whether the object is present or absent transmits a high level signal J when the carton 5 is present, while a low level signal J when the carton 5 is not present. A shift circuit 54 provides the same function as that of displacing the sensor 14 to a position where the electrodes 2, 3 and 4 are situated. A shift value setting circuit 55 outputs the distance S between the sensor 14 and the electrodes 2, 3 and 4 as a set value. The set value causes the shift circuit 54 to output a signal J' which is delayed relative to the signal J by a period of time required for the carton 5 to move the distance S. A gluing length calculation circuit 53 counts the number of the pulse signals N transmitted from the encoder 32 during the output I of the comparison circuit 51 is on H level, to thereby calculate the gluing length P.

With reference to FIG. 7, an average value calculation circuit 56 calculates an average value of the gluing lengths P and produces a reference value to be used for judgement. For instance, the average value calculation circuit 56 calculates an average value Pm of the gluing lengths P measured at fifth one to ninth one from the commencement of checking the glue application state, and determines the thus obtained average value as a reference gluing length. Then, the apparatus in accordance with the invention starts checking the glue application state from a tenth object. An allowable value setting circuit 57 establishes an allowable range ΔP for gluing length. A decision circuit 58 compares the gluing length P with the reference gluing length Pm. If a difference between them is within the allowable range ΔP, the decision circuit 58 admits that the difference is normal, and transmits a low level signal M, while the difference is without the allowable range ΔP, the decision circuit 58 admits the difference is abnormal, and transmits a high level signal M. The output J' of the shift circuit 54 plays a role of gate in the gluing length calculation circuit 53, the average value calculation circuit 56 and the decision circuit 58, and makes the circuits 53 and 58 to calculate the gluing length and make the decision only while the output J' is on high level. A display circuit 59 displays thereon the outputs M transmitted from the decision circuit 58, and in addition, displays warning in the case that the signal M represents the abnormality, namely the signal M is on high level. An output circuit 60 transmits an order for stopping the conveyer belts 30 and 31 illustrated in FIG. 4, when the signal M represents the abnormality.

Figure 8:
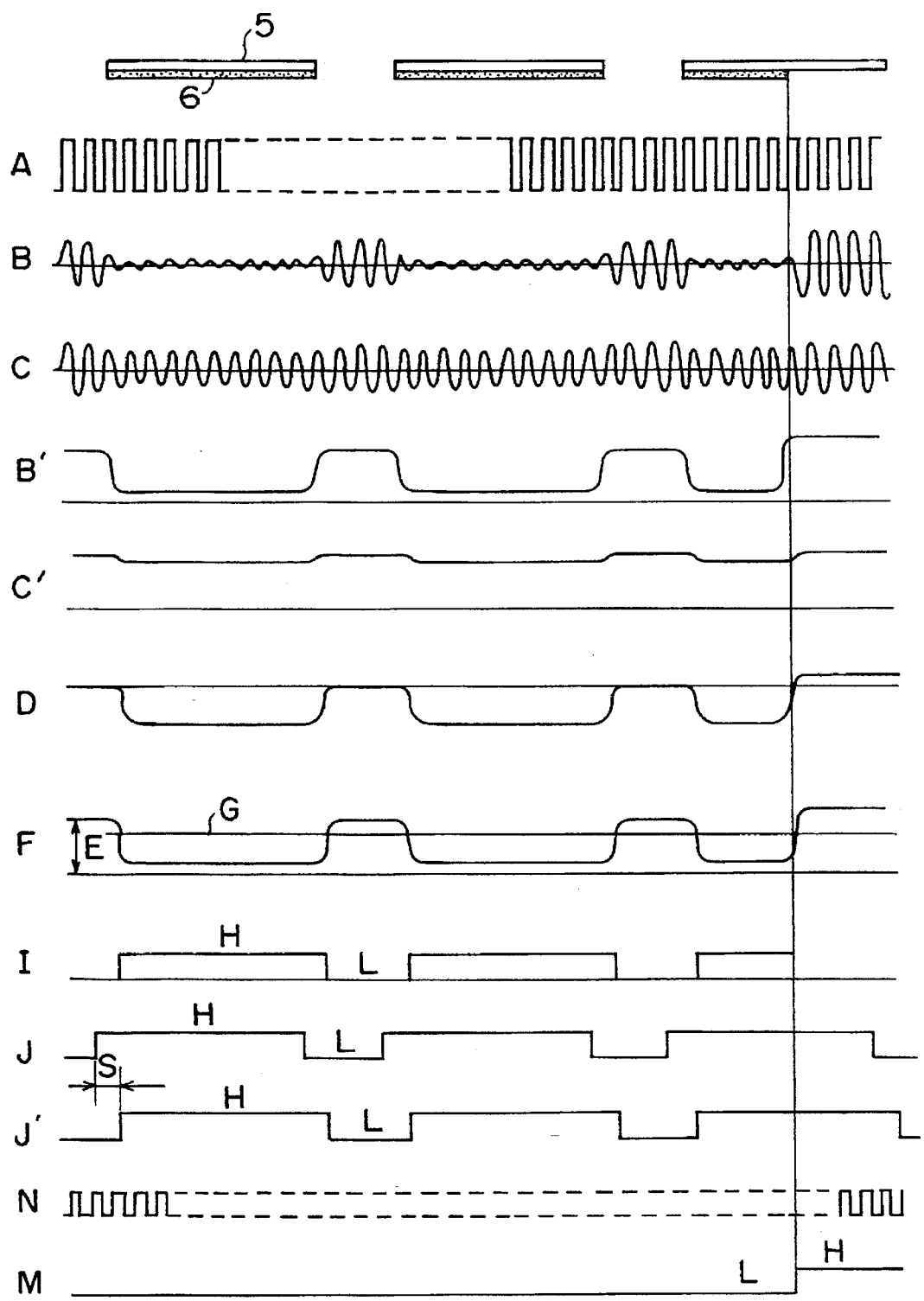
FIG. 8 is a view showing waveforms of each of the signals shown in FIGS. 5 to 7.

FIG. 8 illustrates waveforms of each of the signals shown in FIGS. 5 to 7. The waveforms A to M in FIG. 8 corresponds to the signals A to M shown in FIGS. 5 to 7. The wavefrom A represents an output transmitted from the power amplification circuit 41 and is a high frequency pulse having a constant amplitude. The waveform B represents an output transmitted from the receiving electrode 3 for detection, and would have a smaller amplitude if the glue 6 is applied to the object, because energy is absorbed into the glue 6. The waveform C represents an output of the reference receiving electrode 4, and would have a slightly reduced amplitude even if the glue 6 is present, because the reference receiving electrode 4 is spaced away from the glue 6. The waveform B' represents an output of the gain adjustment circuit 46, the waveform C' represents an output of the low-pass filter circuit 45b, and the waveform D represents an output of the differential amplification circuit 47.

The waveform F represents the curve D to which the bias value E is added so that the waveform F can be properly displayed on the display circuit 50. The waveform G represents a reference value, and indicates that the gluing has been carried out, when the value F is equal to or smaller than the value G. The waveform I represents an output of the comparison circuit 51. When the value F is equal to or smaller than the value G, the output I is on high level indicating that the glue has been applied, while when the value F is over the value G, the output I is on low level indicating that the glue 6 has not yet been applied. The waveform J represents an output of the sensor 14 for detecting whether the object 5 is present or not, and indicates that the object 5 is present when the output J is on high level, while indicates that the object is not present when the output J is on low level. The waveform J' represents an output of the shift circuit 54, and corresponds to the signal J delayed by a period of time required for the object 5 to be fed in the distance S between the sensor 14 and the electrodes 2, 3 and 4. The waveform N represents pulse signals transmitted from the encoder 32, and calculates the gluing length on the basis of the number of pulses produced during the signal I is on high level. M is an output of the decision circuit 58, and would be on high level when a period of time in which the signal I is on high level is shorter than the allowable value.

Figure 9:
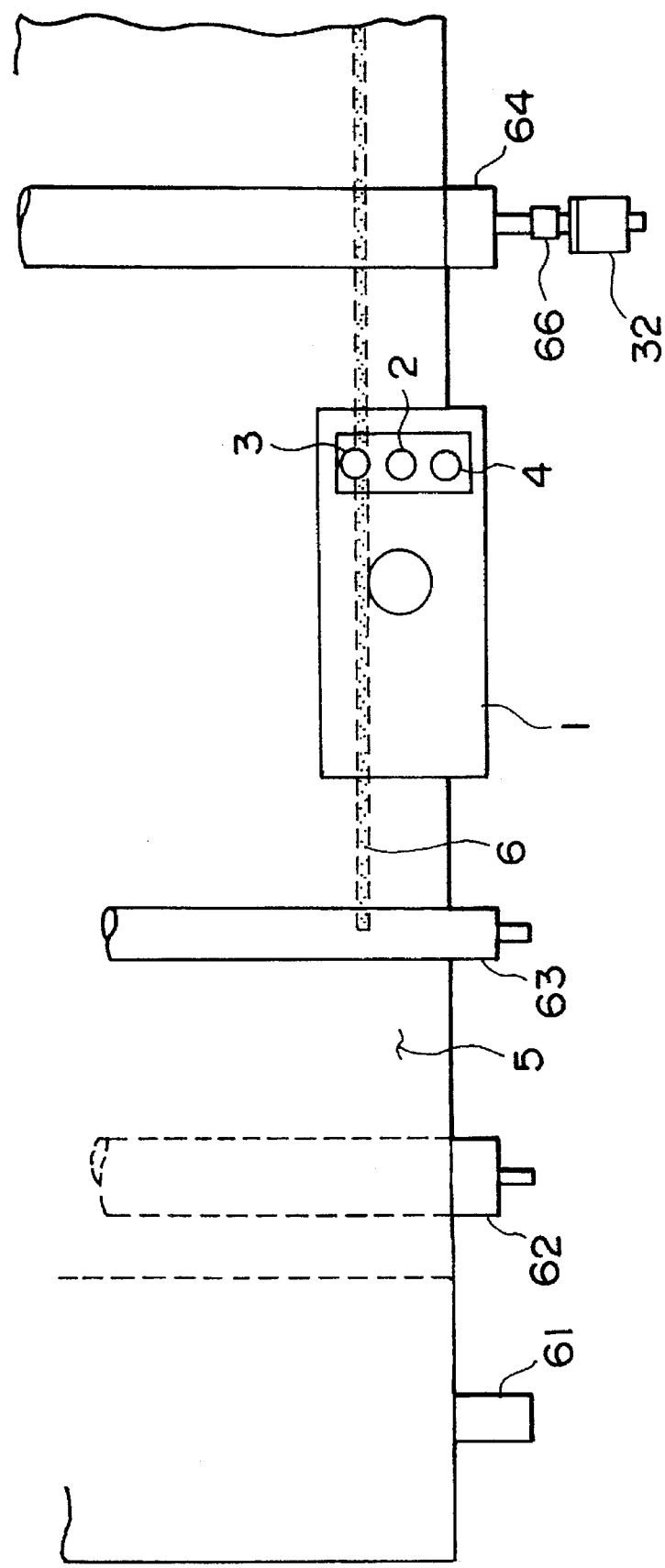
FIG. 9 is a plan view of the apparatus in accordance with the second embodiment.
Figure 10:
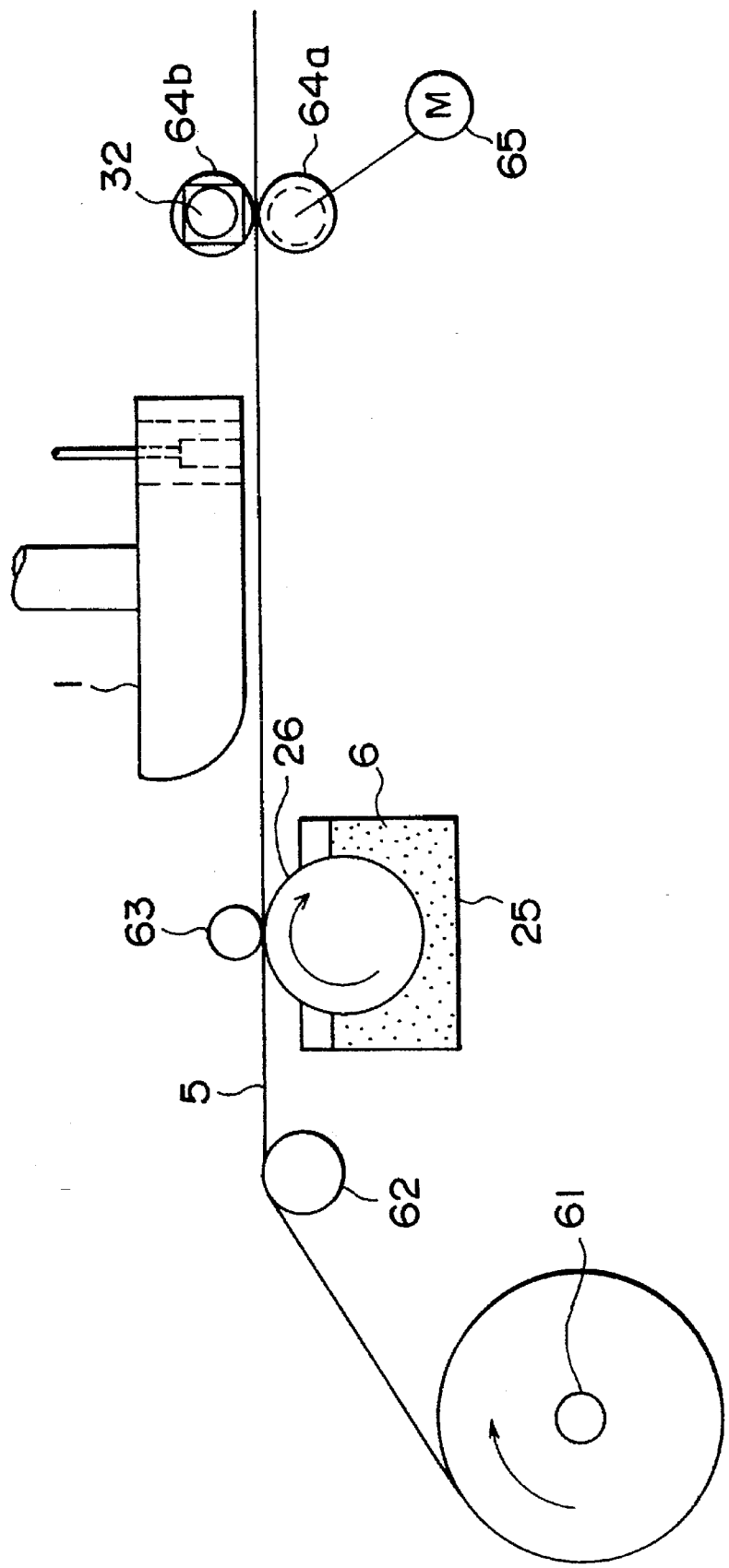
FIG. 10 is a side view of the apparatus illustrated in FIG. 9.

Hereinbelow will be explained the second embodiment. In the second embodiment, the apparatus for checking glue application state in accordance with the invention is applied to a bag-making apparatus or a collator which continuously apply a glue to a continuous paper. FIG. 9 is a plan view of the apparatus in accordance with the second embodiment, and FIG. 10 is a side view of the same. Parts or elements correspond to those of the first embodiment illustrated in FIGS. 1 to 4 have been provided with the same reference numerals. A web 5 unwound from a roll 61, an object to which the glue 6 is to be applied in the second embodiment, is introduced by a guide roll 62 between a glue applicator wheel 26 and a roll 63 to thereby be glued. The thus glued web 5 is fed by a draw roll 64. The draw roll 64 consists of upper and lower rolls. The lower roll 64a is driven to rotate by a drive motor 65. The lower roll 64a has a reduced diameter portion in the vicinity of a glued portion of the web 5 so that the glue 6 does not adhere to the roll 64a. The encoder 32 is connected to a shaft of the upper roll 64b through a coupling 66. The detector head 1 is provided with the high frequency transmitting electrode 2, the receiving electrode 3 for detection and the reference receiving electrode 4, but not provided with the sensor 14 for detecting whether the object is present or not. The detector head 1 can be adjusted horizontally and vertically in position by a position adjuster (not illustrated).

Figure 11:
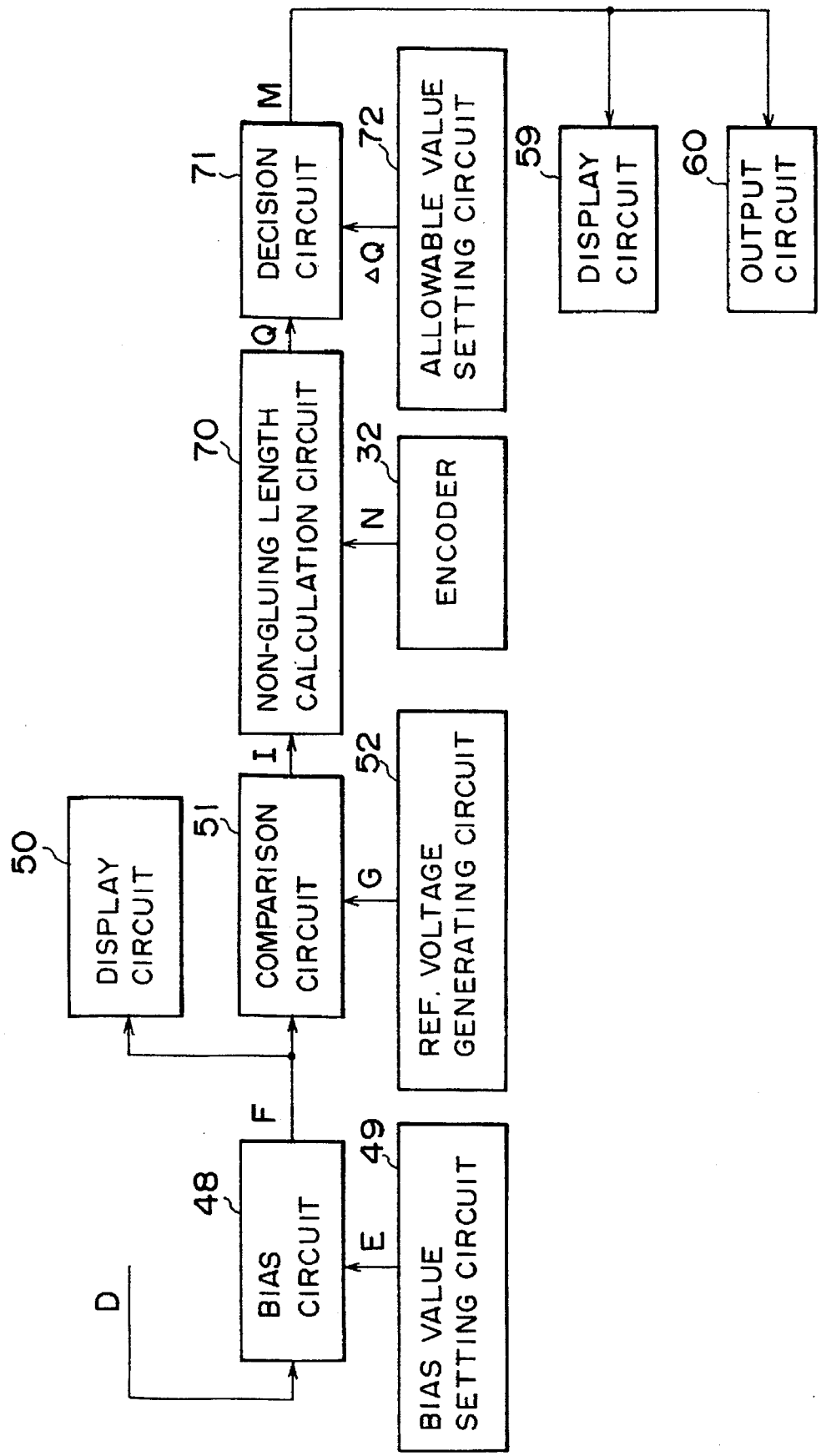
FIG. 11 is a block diagram of the decision circuit and associated circuits therewith in the second embodiment.

FIGS. 1 and 5 are allowed to use for explanation of the second embodiment. FIG. 11 illustrates a circuit for checking glue application state, which is simplified relative to the circuit illustrated in FIGS. 6 and 7. In the first embodiment, an object having the gluing length which does not reach the reference value is determined to be abnormal, while in the second embodiment, an object having a non-gluing length which is in excess of a reference value is determined to be abnormal. In FIG. 11, A non-gluing length calculation circuit 70 starts counting the number of pulses transmitted from the encoder 32 immediately when the output I of the comparison circuit 51 becomes a low level, and thus calculates in real-time a length Q by which the glue 6 is not applied to the web 5. An allowable value setting circuit 72 stores therein a maximum non-gluing length ΔQ. A decision circuit 71 compares the maximum length ΔQ with the length Q calculated in real-time, and changes the output signal M from a low level to a high level when the length Q becomes excess of the maximum length ΔQ. When the output signal M is changed from the low level to the high level, the display circuit 59 displays 'abnormal', and at the same time, the output circuit 60 transmits an order for stopping the drive motor 65 illustrated in FIG. 10.

Figure 12:
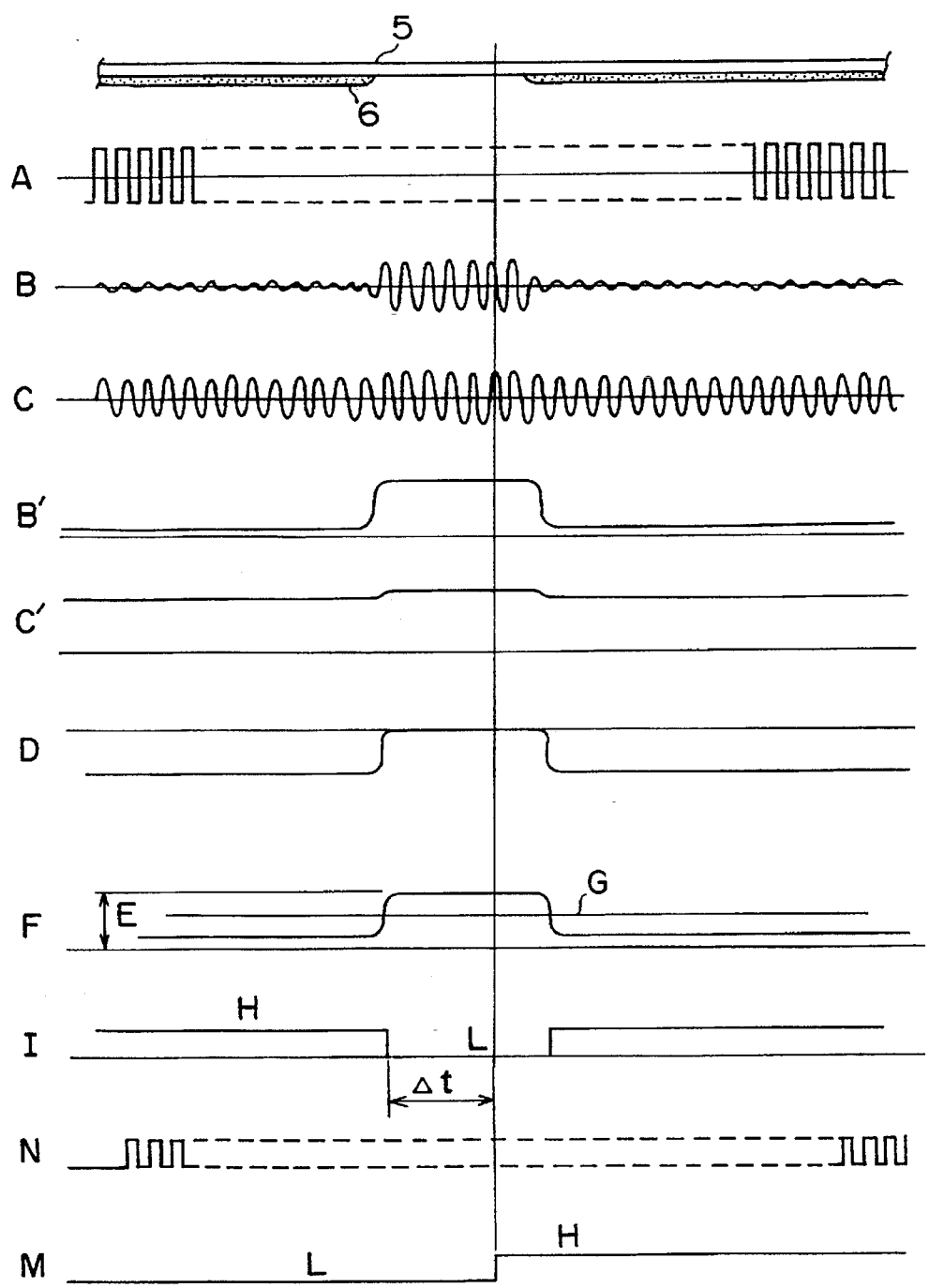
FIG. 12 is a view showing waveforms of each of the signals shown in FIGS. 5 and 11.

FIG. 12 illustrates waveforms of each of the signals shown in FIGS. 5 and 11. The illustrated waveforms A to M correspond to A to M in FIGS. 5 and 11. The waveform A represents an output transmitted from the power amplification circuit 41 and is a high frequency pulse having a constant amplitude. The waveform B represents an output transmitted from the receiving electrode 3 for detection, and would have a smaller amplitude if the glue 6 is applied to the object 5, because energy is absorbed into the glue 6. The waveform C represents an output of the reference receiving electrode 4, and would be influenced by the glue 6 just a little. The waveform B' represents an output of the gain adjustment circuit 46, the waveform C' represents an output of the low-pass filter circuit 45b, and the waveform D represents an output of the differential amplification circuit 47. The waveform F is a curve corresponding to the curve D to which the bias value E is added. The waveform G represents a reference value, and indicates that the gluing has been carried out, when the value F is equal to or smaller than the value G. The waveform I is an output of the comparison circuit 51. When the value F is equal to or smaller than the value G, the output I is on a high (H) level indicating that the glue has been applied, while when the value F is over the value G, the output I is on a low (L) level indicating that the glue 6 has not yet been applied. The waveform N represents pulse signals transmitted from the encoder 32. The non-gluing length calculation circuit 70 counts the number of the pulse signals during the signal I is on the low level, and thus calculates the non-gluing length Q. The length Q becomes longer, as the length of the low level of the signal I varies from moment to moment. When the length Q exceeds the allowable value ΔQ, the output M transmitted from the decision circuit 71 is turned from a low level to a high level. Namely, provided that it takes a period of time Δt for the web 5 to run the maximum length ΔQ, the signal M is changed from the low level to the high level when the length (time) of the low level in the signal I reaches Δt.

Though the glue 6 is to be applied to the object 5 at its lower surface in the first and second embodiments, it is possible to detect whether the glue 6 is applied to the object 5 even if the glue 6 has been applied to the object 5 at its upper surface. However, in this case, since the glue 6 is prone to adhere to the detector head 1, it is necessary to frequently remove the glue 6 off the detector head 1 or to adopt a structure for avoiding the glue 6 from adhering to the object 5. In order to apply a glue to an object, a glue applicator nozzle may be substituted for the glue applicator wheel 26. Instead of arranging the detector head 1 above the object 5, the detector head 1 may be disposed below the object 5. The object 5 may be vertically fed with the detector head 1 being directed horizontally. In the first and second embodiments, the object 5 is composed of a paper, however, it should be noted that the object 5 may be composed of any non-conductive material such as plastic. Though a paper may have slight conductivity due to moisture contained therein, it is possible to check glue application state of a paper object.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An apparatus for checking glue application state of almost electrically non-conductive object to which an electrically conductive glue is applied on either side thereof, said apparatus comprising:

a transmitting electrode for transmitting high frequency therefrom;

a pair of receiving electrodes each spaced away from said high frequency transmitting electrode at its opposite sides;

a detector head, by which said transmitting electrode and receiving electrodes are supported, for aligning distal ends of said electrodes at almost the same level and shielding said electrodes from one another;

a high frequency generator, in electrical connection with said transmitting electrode, for supplying high frequency to said high frequency transmitting electrode; and a glue application state detector, in electrical connection with said receiving electrodes, for detecting glue application state of said object on the basis of a difference in output between said receiving electrodes, said detector heading being supported by a base.

2. An apparatus for checking glue application state of almost electrically non-conductive object to which an electrically conductive glue is applied on either side thereof, said apparatus comprising:

a transmitting electrode for transmitting high frequency therefrom;

a pair of receiving electrodes each spaced away from said high frequency transmitting electrode at its opposite sides;

a detector head, by which said transmitting electrode and receiving electrodes are supported, for aligning distal ends of said electrodes at almost the same level and shielding said electrodes from one another;

a high frequency generator, in electrical connection with said receiving electrodes, for supplying high frequency to said high frequency transmitting electrode;

a glue application state detector for detecting glue application state of said object on the basis of a difference in output between said receiving electrodes; and a position adjuster for adjusting relative position between a glue applied to said object and each of said electrodes, said detector head being supported by a base.

3. The apparatus as set forth in claim 2, wherein said position adjuster adjusts the position of said glue to be applied to said object so that said glue is disposed closer to one of said receiving electrodes than to a middle between said high frequency transmitting electrode and said one of said receiving electrodes.

4. The apparatus as set forth in claim 2, wherein said position adjuster adjusts a distance between distal ends of said electrodes and a surface of said object to which said glue is to be applied.

5. The apparatus as set forth in claim 3, wherein said position adjuster adjusts a distance between distal ends of said electrodes and a surface of said object to which said glue is to be applied.

* * * * *